United States Patent
Wang et al.

(10) Patent No.: US 10,561,394 B2
(45) Date of Patent: Feb. 18, 2020

(54) ULTRASOUND SCANNING AND ULTRASOUND-ASSISTED BIOPSY

(75) Inventors: Shih-Ping Wang, Los Altos, CA (US);
Tor C. Anderson, Los Gatos, CA (US);
Jiayu Chen, Palo Alto, CA (US);
Douglas G. Summers, Palo Alto, CA (US)

(73) Assignee: U-SYSTEMS, INC., San Jose, CA (US)

( * ) Notice: Subject to any disclaimer, the term of this patent is extended or adjusted under 35 U.S.C. 154(b) by 98 days.

(21) Appl. No.: 12/299,275

(22) PCT Filed: May 2, 2007

(86) PCT No.: PCT/US2007/010753
§ 371 (c)(1),
(2), (4) Date: Mar. 19, 2010

(87) PCT Pub. No.: WO2007/130526
PCT Pub. Date: Nov. 15, 2007

(65) Prior Publication Data
US 2010/0174185 A1    Jul. 8, 2010

Related U.S. Application Data

(60) Provisional application No. 60/746,259, filed on May 2, 2006.

(51) Int. Cl.
*A61B 8/08* (2006.01)
*A61B 8/00* (2006.01)
(Continued)

(52) U.S. Cl.
CPC .......... *A61B 8/0825* (2013.01); *A61B 8/0833* (2013.01); *A61B 8/0841* (2013.01);
(Continued)

(58) Field of Classification Search
CPC ......... A61B 8/00; A61B 10/02; A61B 8/0825; A61B 8/54; A61B 2017/2253
(Continued)

(56) References Cited

U.S. PATENT DOCUMENTS 3,964,296 A * 6/1976 Matzuk .................... A61B 8/00
73/607
4,573,452 A * 3/1986 Greenberg .................... 600/102
(Continued)

FOREIGN PATENT DOCUMENTS

WO   WO 2004/030523    *   4/2004
WO   WO2004/049906 A2    6/2004
(Continued)

*Primary Examiner* — James M Kish
(74) *Attorney, Agent, or Firm* — McCoy Russell LLP

(57) ABSTRACT

An apparatus and related methods for ultrasonically scanning a tissue sample are described, the apparatus comprising an ultrasound transducer and a membranous sheet, the membranous sheet compressing the tissue sample, the ultrasound transducer contacting the membranous sheet and ultrasonically scanning the tissue sample therethrough, wherein the membranous sheet has a generally arcuate shape and the ultrasound transducer is movable in a generally arcuate trajectory therealong during the ultrasonic scan. Also described is an apparatus for facilitating a medical procedure, comprising a membranous sheet compressing a tissue sample, an ultrasound transducer contacting the membranous sheet to ultrasonically scan the tissue sample therethrough, and a biopsy guide operably coupled to the ultrasound transducer for maintaining a biopsy instrument in a scan plane of the ultrasound transducer to facilitate a percutaneous biopsy of a lesion located in the scan plane.

48 Claims, 16 Drawing Sheets

(51) Int. Cl.
  *A61B 8/14*     (2006.01)
  *G01S 15/89*    (2006.01)

(52) U.S. Cl.
  CPC .............. *A61B 8/14* (2013.01); *A61B 8/4218*
    (2013.01); *A61B 8/4455* (2013.01); *A61B*
    *8/4461* (2013.01); *A61B 8/4483* (2013.01);
    *A61B 8/54* (2013.01); *G01S 15/8934*
    (2013.01); *A61B 8/4472* (2013.01)

(58) Field of Classification Search
  USPC ................................................. 600/407–480
  See application file for complete search history.

(56) References Cited

U.S. PATENT DOCUMENTS

| | | | | |
|---|---|---|---|---|
| 4,580,451 | A * | 4/1986 | Miwa et al. ..................... | 73/626 |
| 5,078,149 | A * | 1/1992 | Katsumata ........... | A61B 8/4281 |
| | | | | 600/459 |
| 5,660,185 | A | 8/1997 | Shmulewitz et al. | |
| 5,770,801 | A * | 6/1998 | Wang et al. ..................... | 73/644 |
| 5,776,062 | A | 7/1998 | Nields | |
| 6,027,457 | A * | 2/2000 | Shmulewitz ......... | A61B 8/0833 |
| | | | | 600/437 |
| 6,128,523 | A * | 10/2000 | Bechtold et al. ............. | 600/411 |
| 6,876,879 | B2 * | 4/2005 | Dines .................. | A61B 6/0414 |
| | | | | 128/915 |
| 6,970,587 | B1 * | 11/2005 | Rogers ................. | G06T 7/0012 |
| | | | | 128/922 |
| 7,731,662 | B2 * | 6/2010 | Anderson ............ | A61B 8/0825 |
| | | | | 600/437 |
| 7,850,613 | B2 * | 12/2010 | Stribling ....................... | 600/459 |
| 2003/0007598 | A1 * | 1/2003 | Wang .................... | A61B 6/463 |
| | | | | 378/37 |
| 2003/0055471 | A1 * | 3/2003 | Fenn ......................... | A61N 5/02 |
| | | | | 607/101 |
| 2003/0135135 | A1 * | 7/2003 | Miwa ....................... | A61N 7/00 |
| | | | | 601/2 |
| 2004/0010193 | A1 * | 1/2004 | Entrekin .............. | A61B 8/0825 |
| | | | | 600/437 |
| 2004/0015080 | A1 * | 1/2004 | Kelly ................... | A61B 8/0825 |
| | | | | 600/437 |
| 2004/0087851 | A1 * | 5/2004 | Lee ...................... | A61B 8/0825 |
| | | | | 600/407 |
| 2004/0202280 | A1 * | 10/2004 | Besson ........................... | 378/37 |
| 2005/0265518 | A1 * | 12/2005 | Aubel .................... | A61B 6/502 |
| | | | | 378/37 |
| 2005/0283063 | A1 * | 12/2005 | Besson .................. | A61B 6/488 |
| | | | | 600/407 |
| 2006/0132283 | A1 * | 6/2006 | Eberhart et al. ............... | 340/5.2 |
| 2006/0189974 | A1 * | 8/2006 | Penny ................... | A61B 18/042 |
| | | | | 606/34 |
| 2007/0232916 | A1 * | 10/2007 | Waki .................... | A61B 5/6843 |
| | | | | 600/444 |
| 2007/0255126 | A1 * | 11/2007 | Moberg et al. ................ | 600/365 |
| 2007/0258626 | A1 * | 11/2007 | Reiner .................. | A61B 5/1171 |
| | | | | 382/115 |
| 2008/0021317 | A1 * | 1/2008 | Sumanaweera ............... | 600/437 |

FOREIGN PATENT DOCUMENTS

| | | | | |
|---|---|---|---|---|
| WO | WO 2005/104729 | * | 11/2005 | ............... A61B 8/08 |
| WO | WO 2006/030436 | * | 3/2006 | |

\* cited by examiner

ULTRASOUND SCANNING AND ULTRASOUND-ASSISTED BIOPSY

CROSS REFERENCE TO RELATED APPLICATIONS

This application claims the benefit of U.S. Provisional Application No. 60/746,259, filed 2 May 2006, which is hereby incorporated by reference herein.

FIELD

This patent specification relates to medical imaging. More particularly, this patent specification relates to ultrasound scanning and ultrasound-assisted biopsy.

BACKGROUND

Volumetric ultrasound scanning usually involves the movement of an ultrasound transducer relative to a tissue sample and the processing of resultant ultrasound echoes to form a data volume representing at least one acoustic property of the tissue sample. Although several examples herein are presented in the particular context of human breast ultrasound, it is to be appreciated that the present teachings are broadly applicable for facilitating ultrasonic scanning of any externally accessible human or animal body part (e.g., abdomen, legs, feet, arms, neck, etc.). Moreover, although several examples herein are presented in the particular context of mechanized scanning (i.e., in which the ultrasound transducer is moved by a robot arm or other automated or semi-automated mechanism), it is to be appreciated that one or more aspects of the present teachings can be advantageously applied in a handheld scanning context.

Volumetric ultrasound scanning of the breast has been proposed as a complementary modality for breast cancer screening as described, for example, in the commonly assigned US 2003/007598A1 published Jan. 9, 2003, which is incorporated by reference herein. The commonly assigned WO 2004/030523A2 published Apr. 15, 2004, which is incorporated by reference herein, describes a full-field breast ultrasound (FFBU) scanning apparatus that compresses a breast along planes such as the craniocaudal (CC) plane, the mediolateral oblique (MLO) plane, etc., and ultrasonically scans the breast. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast.

Other FFBU scanning devices that compress the breast in other directions, such as in generally chestward or "head-on" directions, are described in one or more of the following commonly assigned applications, each of which is incorporated by reference herein: U.S. Ser. No. 60/565,698 filed Apr. 26, 2004; U.S. Ser. No. 60/577,078 filed Jun. 4, 2004; U.S. Ser. No. 60/629,007 filed Nov. 17, 2004; U.S. Ser. No. 60/702,202 filed Jul. 25, 2005; U.S. Ser. No. 60/713,322 filed Aug. 31, 2005; WO 2005/104729A2 published Nov. 10, 2005; and WO 2005/120357A1 published Dec. 22, 2005.

Among other useful applications, ultrasound imaging systems can be used to facilitate percutaneous biopsy procedures in which a needle or other fine biopsy instrument is used to extract a tissue sample. More specifically, ultrasound imaging systems can be used to locate a lesion and to assist the radiologist in guiding a biopsy instrument to the lesion. In such applications, it is necessary to keep the biopsy needle positioned within the imaged plane in order for it to remain visible on the ultrasound monitor during the procedure. As used herein, the terms radiologist and physician are used interchangeably and generically to refer to medical professionals that analyze medical images and make clinical determinations therefrom, and/or that perform medical procedures under the at least partial guidance of medical imaging systems, it being understood that such person might be titled differently, or might have differing qualifications, depending on the country or locality of their particular medical environment.

Percutaneous ultrasound-guided biopsy of the breast is a procedure that can be quickly performed free-handed by a "skilled" physician, using a hand-held ultrasound imaging system, in an out-patient environment. Because this procedure would take less physician time, it is less expensive than other breast biopsy procedures, such as x-ray guided stereotactic BIOPSY and surgical biopsy. Thus, percutaneous ultrasound-guided biopsy has become a highly popular breast biopsy procedure.

However, this procedure could become even more popular if it were easier to perform. This is because many physicians may find it difficult to do the free-handed procedure, which requires the physician to hold a hand-held ultrasound transducer in one hand and the biopsy needle in the other hand, while looking at both the display monitor and the patient breast (usually placed three feet apart) and trying to visualize simultaneously the thin biopsy needle (approximately 1 mm in diameter) and the breast lesion in the thin (approximately 1 mm thick) scan plane of the ultrasound imaging system.

One type of ultrasound-assisted biopsy guide is described in the commonly assigned U.S. Pat. No. 6,695,786, issued Feb. 24, 2004, which is incorporated by reference herein. Although one or more preferred embodiments are herein presented in the particular context of needle biopsy procedures for the breast such as fine needle aspiration biopsy, core-needle biopsy, vacuum-assisted biopsy, and/or other single-cylinder excision alternatives, it is to be appreciated that one or more aspects of the present teachings can be advantageously applied in a variety of different image-guided surgical contexts.

It would be desirable to facilitate ultrasound scanning of a tissue volume (such as, but not limited to, a breast) in a manner that further improves at least one of image quality, volumetric thoroughness, patient comfort, and overall quickness of the scanning process. It would be further desirable to provide assistance to physicians in performing ultrasound-guided biopsy of the breast. It would be further desirable to provide for ultrasound scanning of a tissue volume in a manner that facilitates at least one of guidance, positioning, and operation of a biopsy instrument. Other issues arise as would be readily apparent to one skilled in the art in view of the present disclosure.

SUMMARY

In one embodiment, an apparatus and related methods for ultrasonically scanning a tissue sample are provided, the apparatus comprising an ultrasound transducer and a membranous sheet, the membranous sheet compressing the tissue sample, the ultrasound transducer contacting the membranous sheet and ultrasonically scanning the tissue sample therethrough, wherein the membranous sheet has a generally arcuate shape and the ultrasound transducer is movable in a generally arcuate trajectory therealong during the ultrasonic scan. Preferably, the membranous sheet comprises one or more of a fabric and a vented membrane that is at least partially porous to a liquid or gel acoustic coupling agent. Alternatively, the membranous sheet may comprise material available under the trade name Mylar® or other non-porous sheet-like material, or may comprise thin, sheet-like versions of solid materials such as 40-mil polycarbonate plastic. The tissue sample is compressed in an at least partially conformal manner toward an underlying anatomical structure during the ultrasonic scan.

In one particular example, the tissue sample may be a breast of a human patient and the underlying anatomical structure may be the patient's rib cage. In the context of ultrasonic scanning in which a transducer scans the breast through a compressing membranous sheet, it has been found advantageous to compress the breast along a generally arcuate surface, and still more advantageous to have the generally arcuate surface positioned to compress the breast conformally toward the rib cage. Among other advantages, volumetric thoroughness and patient comfort are promoted while maintaining good image quality. Also promoted is an ability to better accommodate a variety of different breast sizes ranging from larger fatty breasts to smaller dense breasts.

According to another embodiment, an apparatus for facilitating a medical procedure is provided, comprising a membranous sheet compressing a tissue sample, an ultrasound transducer contacting the membranous sheet to ultrasonically scan the tissue sample therethrough, and a biopsy guide operably coupled to the ultrasound transducer for maintaining a biopsy instrument in a scan plane of the ultrasound transducer to facilitate a percutaneous biopsy of a lesion located in the scan plane. The ultrasound transducer is preferably translatable along a scanning trajectory as it scans the tissue sample through the membranous sheet, to provide for volumetric imaging of the tissue sample so that a position of the lesion within the tissue sample can be determined prior to the percutaneous biopsy. In one particular example, the tissue sample is a human breast and the biopsy instrument is a biopsy needle for fine needle aspiration biopsy, core-needle biopsy, or vacuum-assisted biopsy. However, it is to be appreciated that one or more aspects of the present teachings can be advantageously applied for other single-cylinder excision alternatives and in other image-guided surgical contexts.

For one embodiment, the ultrasound transducer is movably disposed within a housing, and the biopsy guide is coupled to the ultrasound transducer through an opening in the housing. The biopsy guide is thereby movable with the ultrasound transducer and maintainable in the scan plane for many or all transducer positions along the scanning trajectory.

In one embodiment, the biopsy guide is provided as an addable and removable accessory to the above-described curved-membrane ultrasonic scanning apparatus. For this embodiment, and with particular applicability to the breast, the part of the tissue sample near an apex of the scanning trajectory becomes raised relative to the other parts of the tissue sample, and side entry of the needle or other biopsy instrument into that raised portion of the tissue sample becomes particularly convenient. In other embodiments, the biopsy guide is provided as an addable/removable accessory for ultrasound scanners having planar (i.e., flat, non-curved) compression surfaces that compress the breast in a generally chestward direction. In still other embodiments, the biopsy guide is provided as an addable/removable accessory for dual compression-plate scanning devices. For another preferred embodiment applicable to each of these cases, the biopsy guide is configured such that the biopsy instrument can have different angular orientations within the scan plane, such as by using a multi-link assembly analogous to that described in the commonly assigned U.S. Pat. No. 6,695,786, supra.

DETAILED DESCRIPTION

Figure 1:
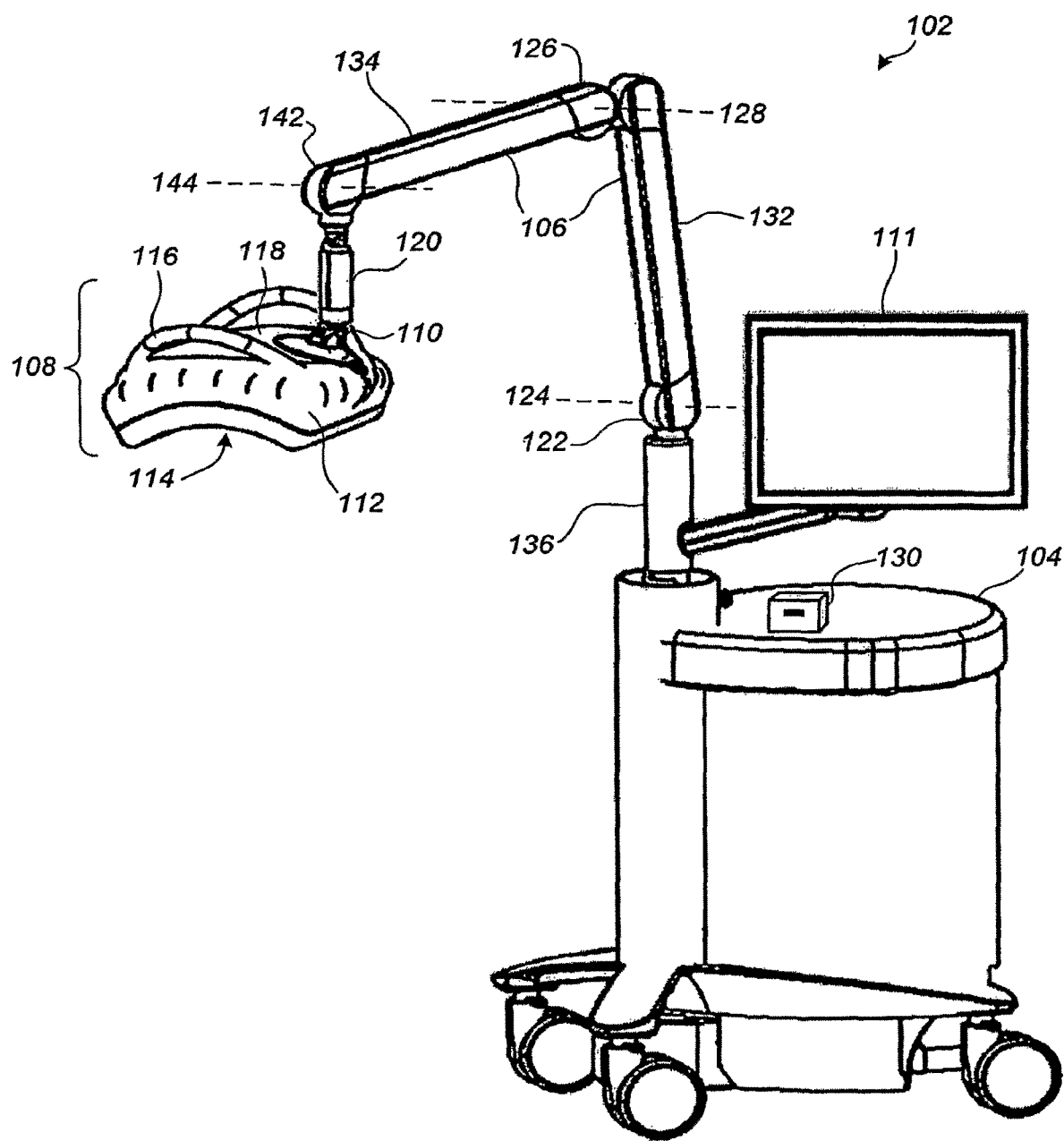
FIG. 1 illustrates a perspective view of a breast ultrasound scanning apparatus according to an embodiment.

FIG. 1 illustrates a perspective view of a breast ultrasound scanning apparatus 102 according to an embodiment, comprising a frame 104 that may contain an ultrasound processor including beamforming electronics, and other processors and electronics including user interface devices and processors, data management and control, and power supplies, a movable support arm 106, a compression/scanning assembly 108 connected to the support arm 106 via a ball-and-socket connector 110, and a monitor 111 connected to the frame 104 as shown. A housing 112 supports a membranous sheet 114 that is disposed across a bottom opening thereof and that compresses the breast, usually toward the rib cage. An ultrasound transducer inside the housing 112 is swept across the top of the membranous sheet 114 in a generally arcuate trajectory to ultrasonically scan the compressed breast therethrough. A top surface 118 of the compression/scanning assembly 108 is preferably translucent to visible light to allow the user to see therethrough and onto the top of the membranous sheet 114, for facilitating ease of positioning. For embodiments in which the membranous sheet 114 is also translucent to visible light, the skin of the compressed breast can itself be seen through the top surface 118.

Preferably, the support arm 106 is configured and adapted such that the compression/scanning assembly 108 is either neutrally buoyant in space, or has a relatively light net downward weight for breast compression, while allowing for easy user manipulation. According to one embodiment, the amount of net downward force exerted onto the patient can be user-adjusted and maintained using actuation and feedback control devices. For example, the user may set the downward force for "8 pounds", and the net amount of downward force maintained (at joint 110, for example) would be automatically maintained at 8 pounds.

According to another embodiment, the current position of the support arm 106 and compression/scanning assembly 108 can be substantially stabilized or "frozen" preferably at the press of a single button (not shown) located near a handle 116 or a foot pedal (not shown). This can be achieved by stepper motors that actuate the support arm 106, or by any of a variety of electronically controlled seizing mechanisms operating at the various joints of the support arm 106. In one embodiment, the positional freezing or stabilization can be absolute, wherein the compression/scanning assembly 108 is kept absolutely at the fixed position and orientation regardless of any forces applied or released subsequent to freezing. In another embodiment, the positional freezing can be non-absolute with a constant downward force, wherein the compression/scanning assembly 108 is kept generally at the fixed or "frozen" position, but wherein a small amount of vertical movement is allowed so as to keep the downward force on the breast constant at the "frozen" amount. The latter embodiment is particularly advantageous because it allows the patient to breathe while at the same time curbing the amount of resulting disturbance to the imaging and/or biopsy procedures being performed.

Support arm 106 is comprised of arm section 132 that is attached to support column 136 via joint 122 such that section 132 can both rotate about the axis of column 136 and about axis 124 of joint 122. Arm section 134 is attached to section 132 via joint 126 so as to allow rotation about axis 128 of joint 126. Section 134 is also attached to column 120 via joint 142 so as to allow movement about axis 144 of joint 142. According to an embodiment arm sections 132 and 134, and joints 122, 126 and 142 are constructed in a four-bar link arrangement that maintains columns 120 and 136 substantially parallel. Neutral buoyancy of compression/scanning assembly 108 so as to allow ease of positioning of assembly 108 upon the patient is preferably achieved using hydraulic cylinders within arm sections 132 and 134. The hydraulic cylinders are preferably electronically lockable using solenoid actuated locking valves. In this way, column 120 can be substantially frozen or fixed along the axis of column 120 electronically. It has been found that locking of arm 106 about the axis of column 136 is not critical in many applications. However, in applications where such movement stabilization is needed, an additional electronically actuated clamp is added within column 136.

Scanning consistency is important ultrasound breast imaging in a number of ways. First, it is important that a scanning system be capable of generating a good image generally free of artifacts due to relative movements between the ultrasound transducer and the patient's breast. Second, it is important that scans of a patient at one time are consistent with scans of the same patient at a later date, thus allowing for useful temporal comparisons. Finally, it is important that a scanning system achieves relatively consistent scans between different patients. It has been found a scanning system in which applies a relatively constant force on the patient's breast during ultrasound scanning, in a direction towards the patient's chest wall is useful in achieving the types of scanning consistency described above. In order to provide for relatively constant force during scanning, a low spring constant of mechanical scanning system in the direction of the patent's chest wall is desirable. In the example shown in FIG. 1, the spring constant of the scanning system includes the flexibility of arm sections 132, 134, columns 136 and 120, and joints 122, 126, 142 and 110. It has been found that a spring constant of less than 100 lbs/inch (17.52 N/mm) is desirable for most applications. According to embodiments, the mechanical scanning system is arranged and designed such that it has a spring constant that preferably is less than 25 lbs/inch (4.38 N/mm). According to an even further preferred embodiment, the scanning system is arranged and designed such that is has a spring constant in the direction towards the chest wall of the patient of less than about 2 lbs/inch (0.35 N/mm).

Column 120 is attached to assembly 108 via locking ball joint 110. According to certain embodiments, column 120 also provides linear actuation (e.g., telescoping) along the axis of column 120. It has been found that in many applications, applying such linear actuation in column 120 provides sufficient net downward force if the actuation occurs after the compression/scanning assembly 108 is correctly positioned on the patient's breast and arm 106 and ball joint 110 are locked. With the spring constant designed into the scanning system as described above, the amount of force can be controlled by the amount of linear actuation of column 120. Further detail of the design of column 120 is provided below with respect to FIG. 17. In still other embodiments, the compression/scanning assembly 108 is not supported by the support arm 106 or other support mechanism, but instead is handheld by the operator. Optionally, battery power and wireless communication technology can be used to make the compression/scanning assembly 108 entirely tether-free.

Optionally, the support arm 106 may comprise potentiometers (not shown) to allow position and orientation sensing for the compression/scanning assembly 108, or other types of position and orientation sensing (e.g., gyroscopic, magnetic, optical, radio frequency (RF)) can be used. Within frame 104 may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

According to certain embodiments, sensor 130 is provided to aid in operator log-in procedures and to increase security. Sensor 130 can be a smart card reader which is adapted to scan the identification badge of the operator. The system can be programmed to automatically load and display the operator's preferred system setup. Sensor 130 can alternatively be implemented as an RFID reader that communicates with the operator's RFID tag, or it may be any of a number of known biometric sensors such as a fingerprint scanner. Sensor 130 can also be integrated into monitor 111.

Figure 2:
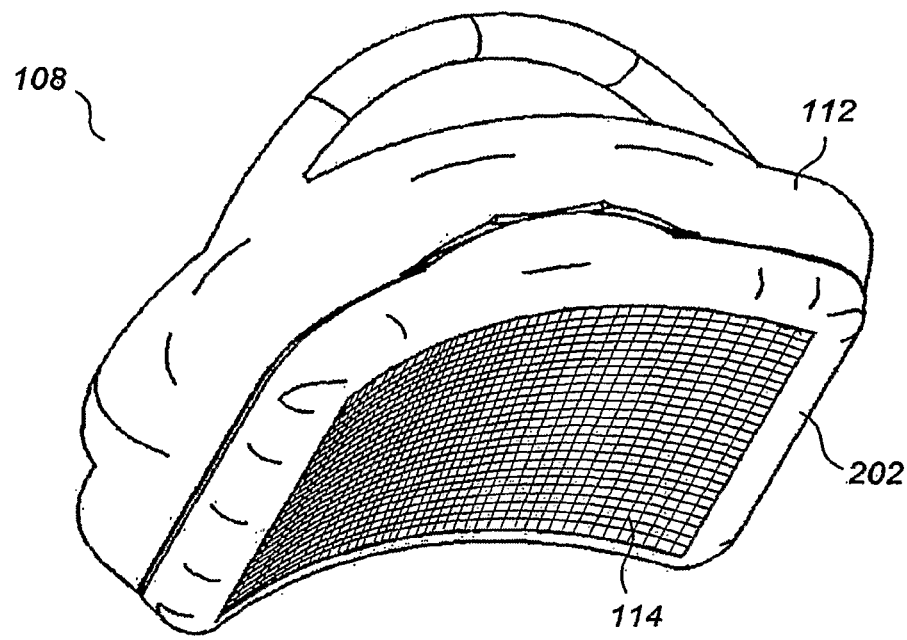
FIGS. 2-3 illustrate a perspective view of a compression/scanning assembly of the ultrasound scanning apparatus of FIG. 1.

FIG. 2 illustrates a perspective view of a bottom of the compression/scanning assembly 108. Preferably, the membranous sheet 114 is disposed across a rigid frame 202 that is removably coupled to the housing 112. The membranous sheet 114 comprises one or more of a fabric (as described in Ser. No. 60/702,202, supra) and a vented membrane (as described in Ser. No. 60/713,322, supra) that is at least partially porous to a liquid or gel acoustic coupling agent. Alternatively, the membranous sheet may comprise Mylar® or other non-porous sheet-like material, or may comprise thin, sheet-like versions of solid materials such as 40-mil polycarbonate plastic. When the compression/scanning assembly 108 is not compressing a breast, the degree of tautness of the membranous sheet 114 will depend on the specific characteristics of the material used. For non-elastic or minimally elastic materials, the membranous sheet 114 may have very low tautness when the compression/scanning assembly 108 is not compressing a breast.

Figure 3:
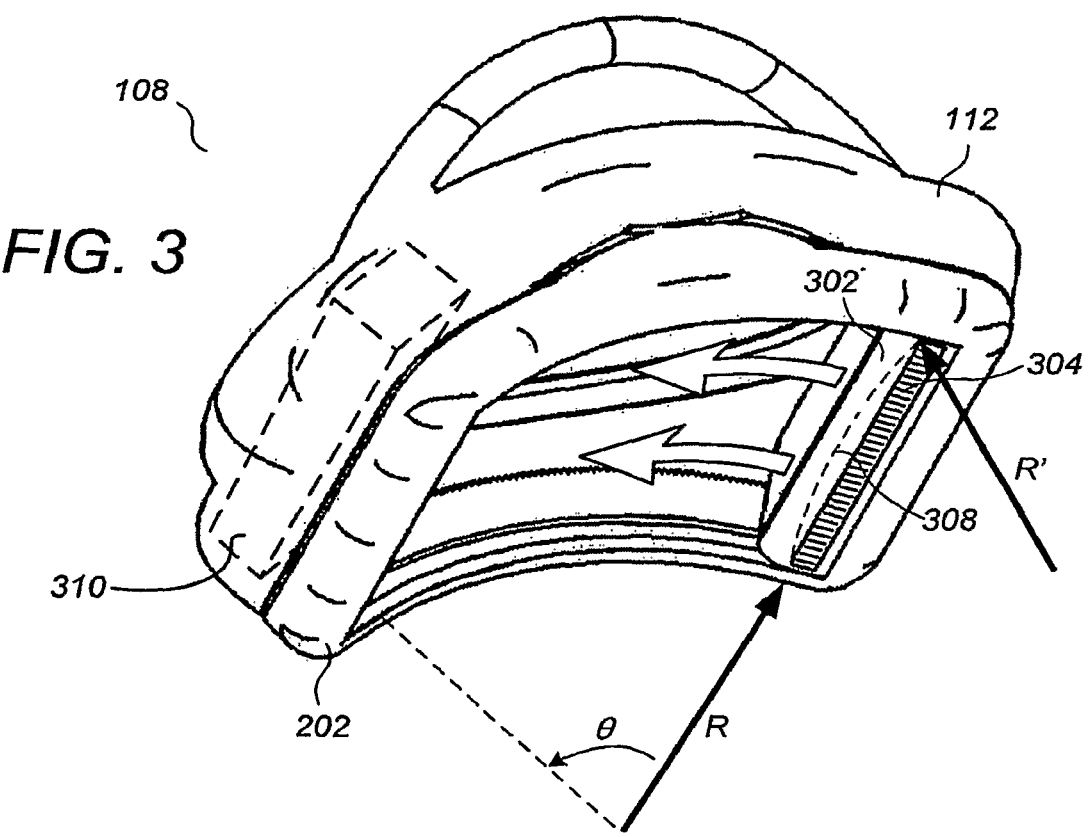

FIG. 3 illustrates a perspective view of a bottom of the compression/scanning assembly 108, with the membranous sheet 114 omitted to display overlying elements. More particularly, an ultrasound probe 302 including a 15-cm, 768-element linear transducer array 304 is provided that sweeps across the breast in an arcuate scanning trajectory. For one preferred embodiment, the arcuate scanning trajectory is roughly circular, such that the surface traversed by the linear transducer array 304 resembles a cylindrical sector having a radius R and a subtended angle θ. In one embodiment, the radius R is between about 6 inches and 36 inches, and the subtended angle θ is between 45 degrees and 135 degrees. In another embodiment, the radius R is between 8-18 inches. In yet another embodiment, the radius R is about 12 inches. In yet another embodiment, the radius R is about 8 inches and the subtended angle θ is about 105 degrees. In other embodiments, the arcuate shape can be elliptical, hyperbolic, or with a profile reminiscent of any of a variety of other shapes that have at least one apex and at least one downward-facing concavity.

According to certain embodiments, the lower face of transducer array 304 is concave as indicated by broken line 308 having radius R'. With a concave face, transducer array 304 can move along a more linear direction while still creating a cylindrical surface. In other words, the radius R as shown in FIG. 3 can be larger. In some embodiments the radius R is greater than 36 inches, or is essentially infinite (i.e. there is no arc along the direction of motion of transducer array 304. In cases where the transducer array is both concave and moves in an arcuate trajectory, an approximately spherical scanned surface (radius R is about equal to radius R') or ellipsoidal scanned surface can be generated.

According to certain embodiments, compact ultrasound electronics 310, including ultrasound beamformer electronics is integrated into compression/scanning assembly 108. Examples of compact ultrasound electronics include products commercially available from Terason, A Division of Teratech Corporation, a corporation of Massachusetts. Placing the ultrasound electronics 310 in compression/canning assembly 108 allows for a much shorter path between electronics 310 and transducer array 304 compared with the electronics positioned in frame 104 as shown in FIG. 1.

Figure 4:
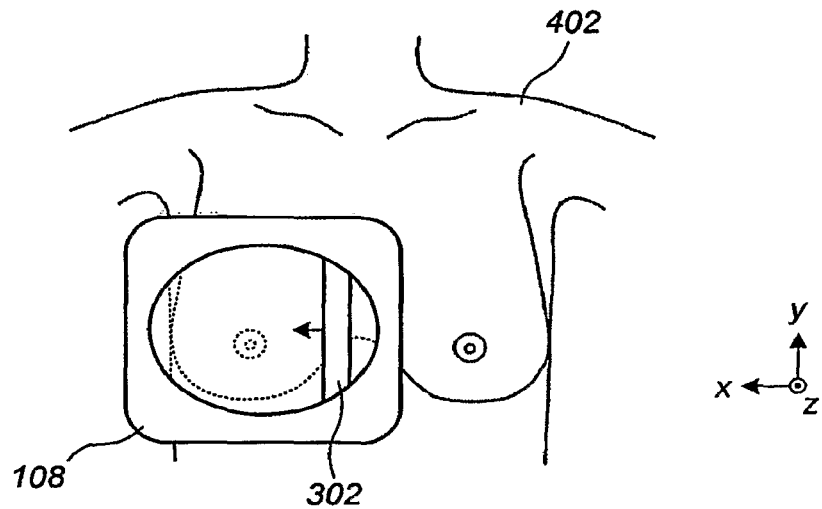
FIGS. 4-5 illustrate a top view of breast ultrasound scanning according to an embodiment.
Figure 5:
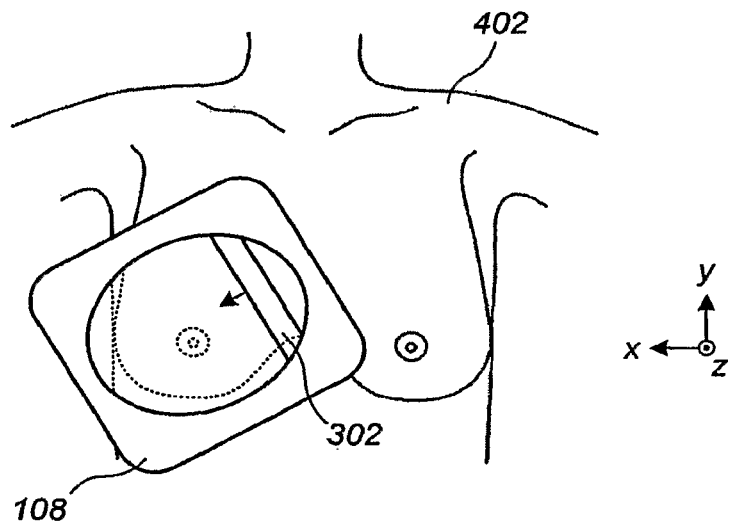

FIGS. 4-5 illustrate a top view of breast ultrasound scanning according to an embodiment. Generally speaking, the arcuate contour of the compression/scanning assembly 108 will be positioned to follow the rib cage of the patient, although a variety of other orientations are possible depending on the breast size, breast shape, and other factors. Thus, while the concavity of the scanning surface and corresponding scanning direction will most commonly point in the range of 0 degrees to 40 degrees relative to the x-z plane in FIGS. 4-5, the range of possibilities is within the full range of rotation around the z-axis in FIGS. 4-5.

Figure 6:
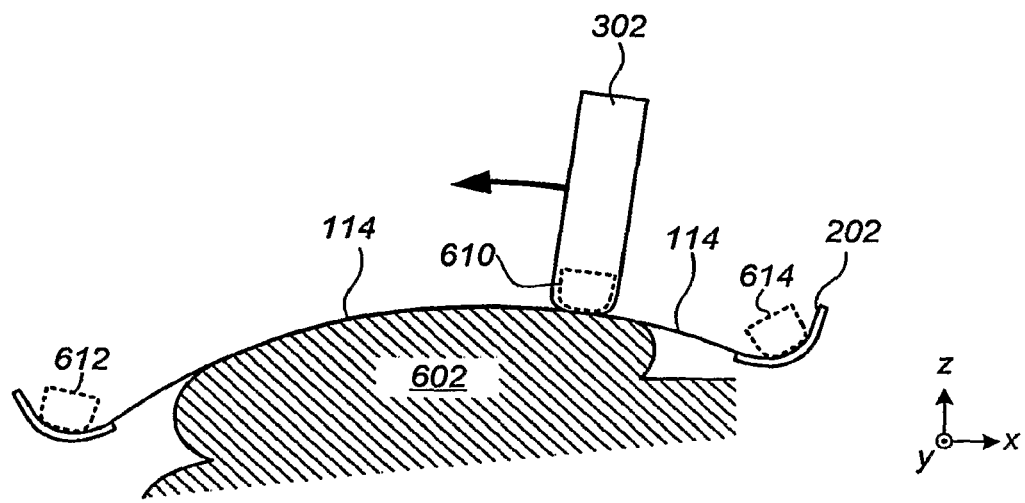
FIGS. 6-7 illustrate an axial cut-away view of breast ultrasound scanning according to an embodiment.
Figure 7:
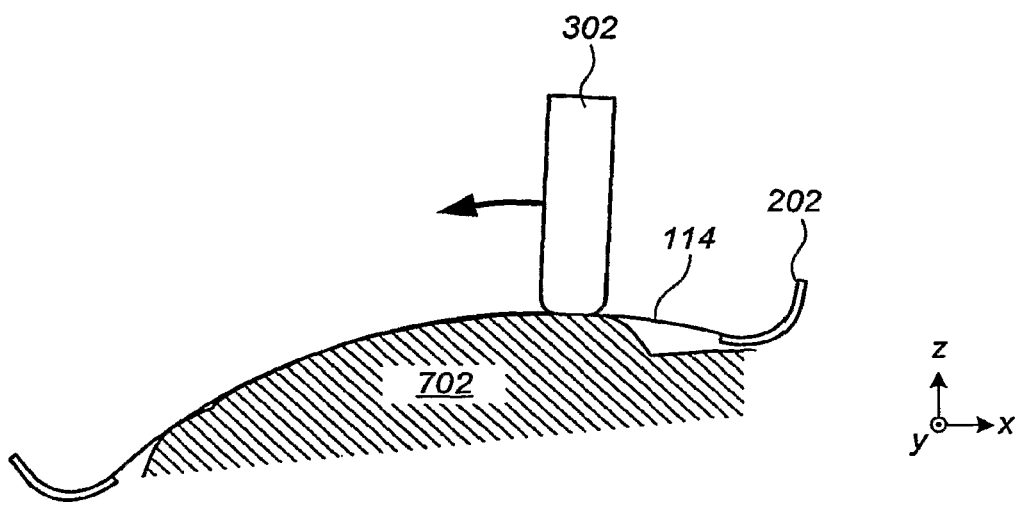

FIG. 6 illustrates an axial cut-away view of a relatively large breast 602 being scanned by the compression/scanning assembly 108, while FIG. 7 illustrates an equivalent view for a relatively small breast 702. As illustrated in FIGS. 6-7, it has been found that the at-least rough conformality of the compression and scanning surface to the shape of the rib cage can provide for more thorough volumetric scanning for a larger variety of breast sizes and shapes. According to certain embodiments, pressure sensors are included within compression/scanning assembly 108. In FIG. 6, pressure sensor 610 is integrated with the transducer array 302 and is preferably a piezo-electric type pressure sensor, although other types of sensors could be used including strain gauges and/or MEMs bases pressure sensors. Pressure sensor 610 measures the pressure being applied to the patient's breast by transducer array 302, thereby aiding in scanning consistency. A feedback control loop can be added with the stepper motor within column 120 (described infra with respect to FIG. 17) so as to provide a more constant force to the patient's breast, thereby further increasing consistency of scans. Sensor 610 can also be linked to an audio and/or visual indicator that aids the operator in correct positioning and pressure of compression/scanning assembly 108. Also shown in FIG. 6 are alternative locations 612 and 614 for sensors which are mounted on the sides of compression/scanning assembly 108 in order to measure the tension on membrane 114.

Figure 8:
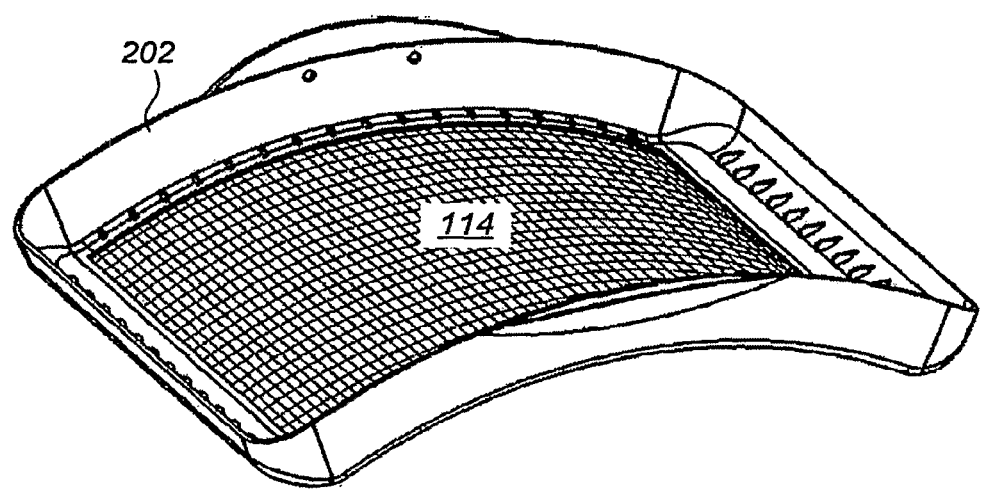
FIG. 8 illustrates a perspective view of a curved frame and membranous sheet as removed from a compression/scanning assembly according to an embodiment.

FIG. 8 illustrates a perspective view of the curved frame 202 and membranous sheet 114 affixed thereto as removed from a compression/scanning assembly according to an embodiment. The curved frame 202 is designed to easily snap in and out of the housing 112 of the compression/scanning assembly 108. In one embodiment, the curved frame 202 and membranous sheet 114 are permanent or semi-permanent components of the overall apparatus and are sterilized after each patient. In another embodiment, the curved frame 202 and membranous sheet 114 are disposable or recyclable and are replaced after each patient.

Figure 9:
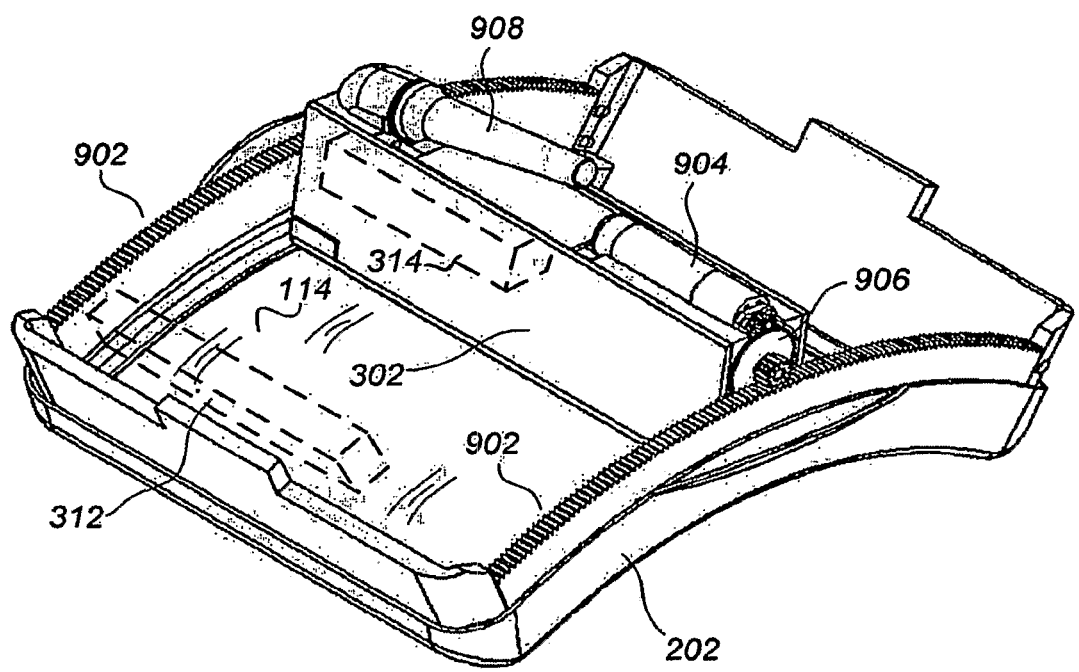
FIG. 9 illustrates a perspective view of an ultrasound transducer, a curved membranous sheet, a rigid frame, and a transducer translation apparatus according to an embodiment.

FIG. 9 illustrates a perspective view of the membranous sheet 114 and the curved frame 202 in conjunction with the ultrasound probe 302. Also shown in FIG. 9 is a probe translation assembly comprising rigid, curved racks 902, a motor 904, and a gear/pinion 906 configured such that the ultrasound probe 302 moves along the curved racks 902 according to actuation of the motor 904. Also shown in FIG. 9 is a connector 908 that connects to electrical cabling driving the transducer elements. It is to be appreciated that many different mechanical configurations achieving similar mechanical goals would be apparent to one skilled in the art in view of the present disclosure and are within the scope of the embodiments. Also shown in FIG. 9 are alternative locations 312 and 314 for compact ultrasound electronics 310 as described in connection with FIG. 6 supra.

Figure 10:
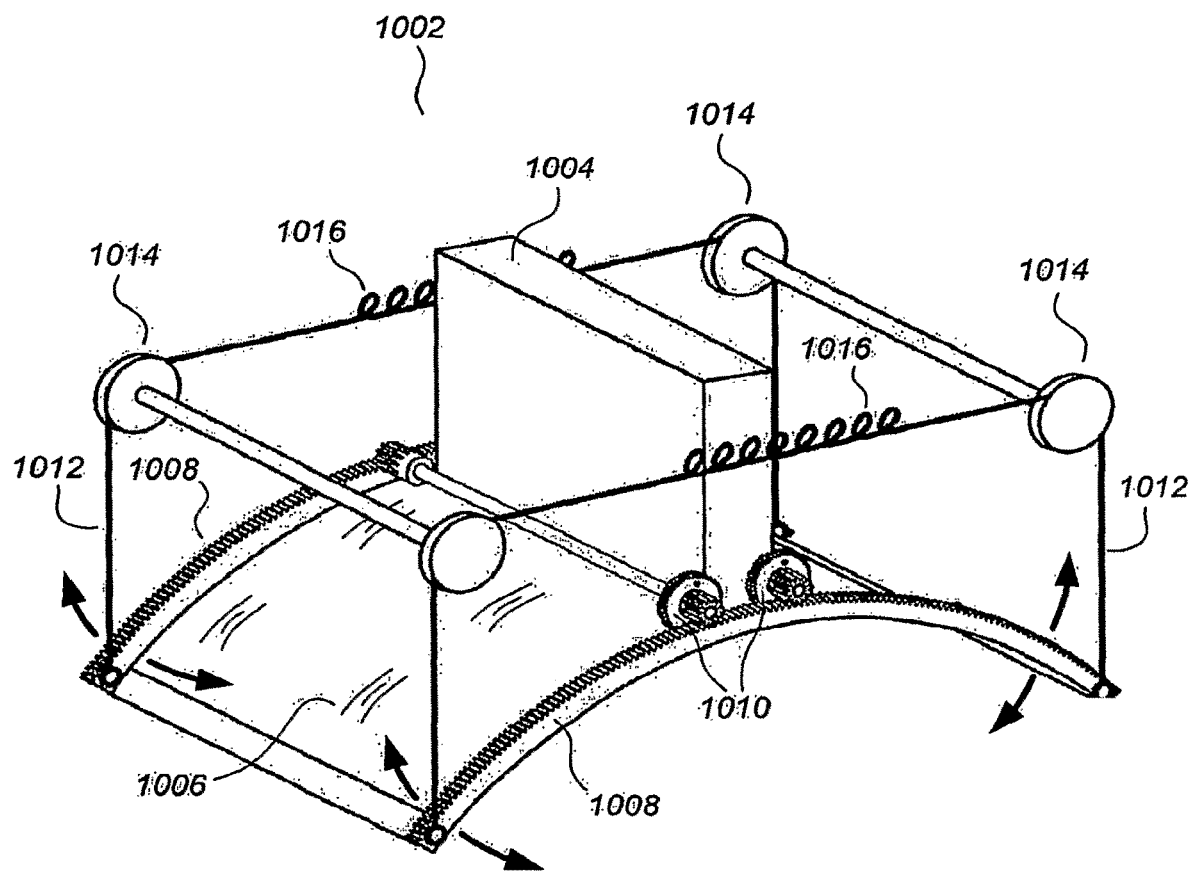
FIG. 10 illustrates a perspective view of a flexible curved compression/scanning assembly according to an embodiment.

FIG. 10 illustrates a perspective view of a flexible curved compression/scanning assembly 1002 for which the particular shape of the compression surface can vary according to the particular body part being compressed and the forces being applied. An ultrasound probe 1004 is mechanically swept across a curved membranous sheet 1006 that is disposed across a frame, the frame being conformal with two flexible racks 1008. The two flexible racks 1008 are themselves used in conjunction with multiple motor-driven pinions 1010 to translate the ultrasound probe 1004 (the motors are not shown). The flexible assembly is mechanically supported and stabilized by wires 1012 coupled to pulleys 1014 secured to assembly 108, and springs 1016 as shown, to selectively change the curvature of racks 1008. It is to be appreciated that many different mechanical configurations achieving similar mechanical goals would be apparent to one skilled in the art in view of the present disclosure and are within the scope of the embodiments.

Figure 11:
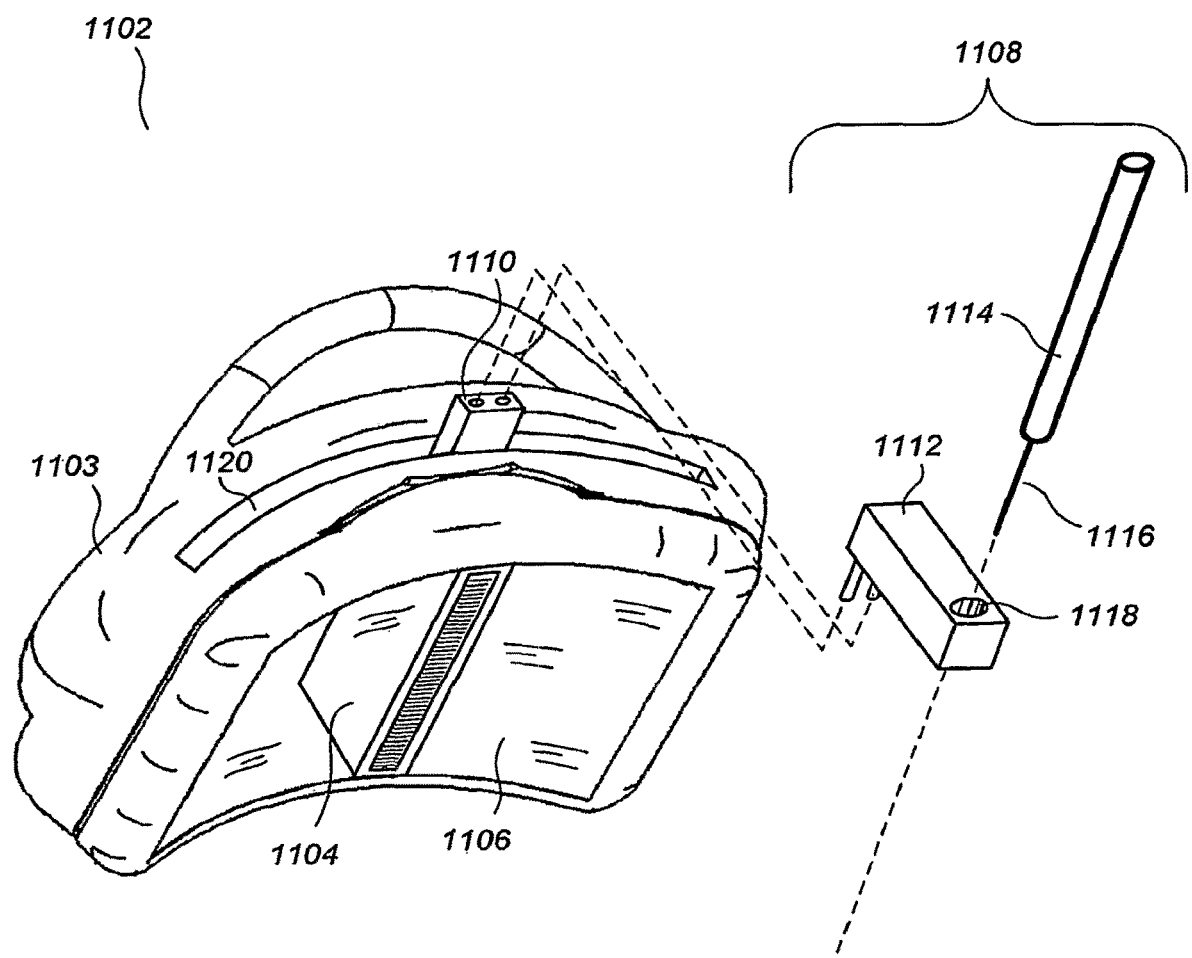
FIG. 11 illustrates a perspective view of a compression/scanning assembly and a biopsy attachment according to an embodiment.
Figure 12:
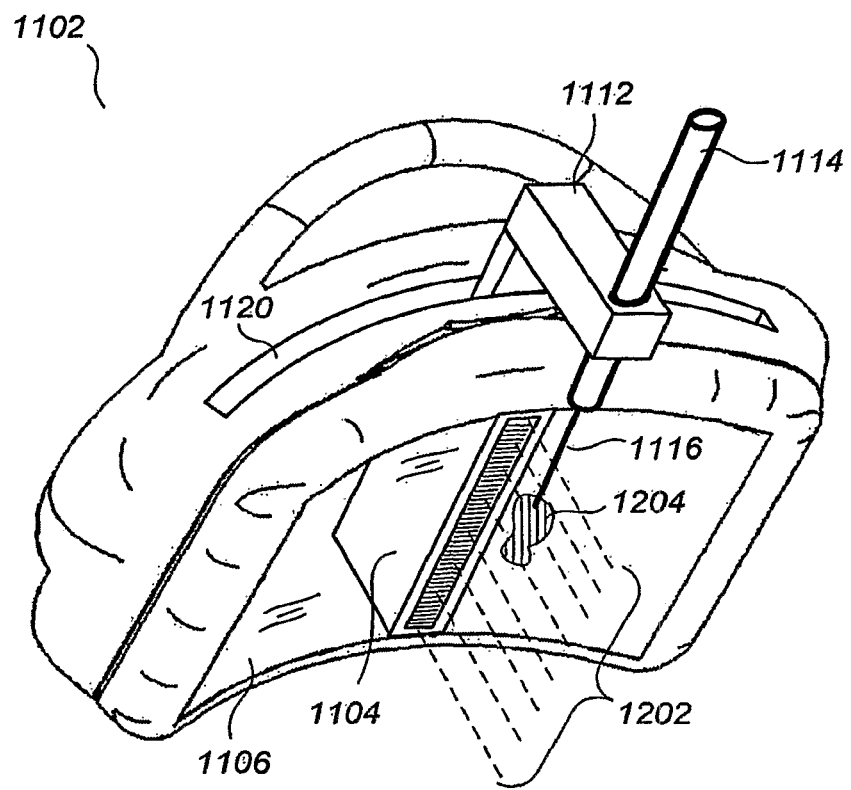
FIG. 12 illustrates a conceptual perspective view of the biopsy guide of FIG. 11 guiding a biopsy instrument into a lesion located in a scan plane of an ultrasound transducer.

FIGS. 11-12 illustrate a perspective view of a compression/scanning assembly 1102 and a biopsy attachment 1108 according to an embodiment. An ultrasound probe 1104 is mechanically swept in an arcuate trajectory across a curved membranous sheet 1106 disposed across a bottom opening of a housing 1103, in a manner similar to that shown for FIGS. 2-3, supra. A coupler 1110 is affixed to the ultrasound probe 1104 through a slot 1120 formed in the housing 1103, the slot 1120 having the same shape as the arcuate trajectory of the ultrasound probe 1104. The biopsy attachment 1108 comprises a guide 1112 and a biopsy instrument comprising a needle holder 1114 and a biopsy needle 1116. A biopsy guide is formed when the guide 1112 is inserted into the coupler 1110, the biopsy guide restricting the biopsy needle 1116 to a scan plane 1202 that intersects a lesion 1204 during the biopsy procedure.

Preferably, the guide 1112 is extendable in a lengthwise direction such that the depth of the biopsy instrument into the scan plane (i.e., the downward distance from the linear transducer array within the scan plane in FIGS. 11-12) can be varied. By way of example, the guide 1112 may be provided with a telescoping and retracting capability, analogous to that of a retractable radio antenna. Alternatively, a selection of guides 1112 of different lengths can be provided so that a suitable guide can be used for each patient. It is to be appreciated that many different mechanical configurations achieving similar mechanical goals would be apparent to one skilled in the art in view of the present disclosure and are within the scope of the embodiments, including embodiments with motorized positioners and needle insertion mechanisms.

Figure 13:
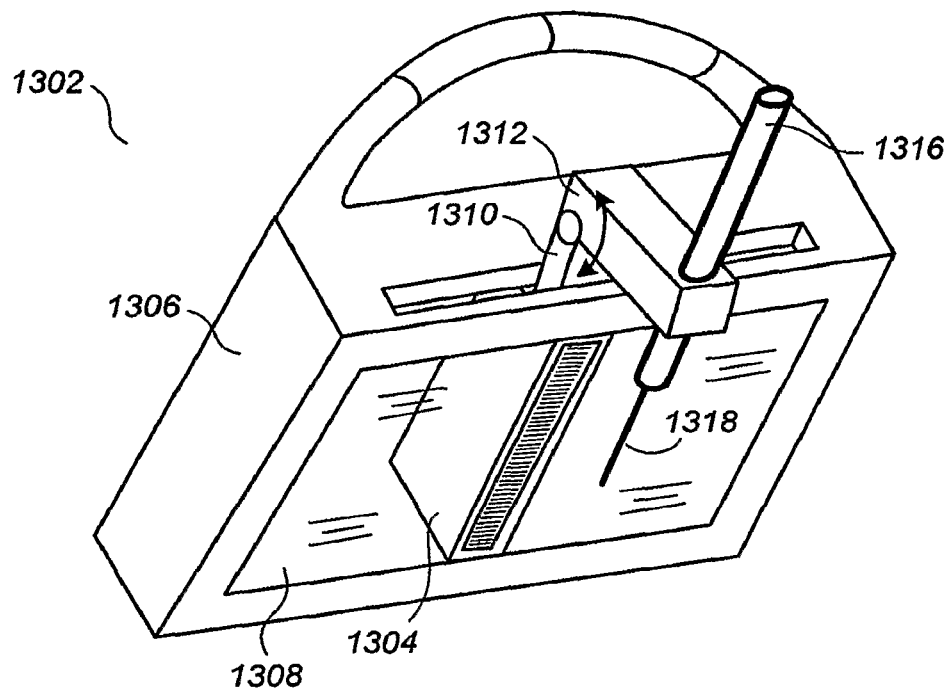
FIG. 13 illustrates a perspective view of a compression/scanning assembly and a biopsy guide attachment according to an embodiment.

FIG. 13 illustrates a perspective view of a compression/scanning assembly 1302 and a biopsy guide 1310/1312 according to an embodiment. An ultrasound probe 1304 is mechanically swept in a flat, planar trajectory across a flat membranous sheet 1308 disposed across a flat bottom opening of a housing 1306, in a manner similar to that described in Ser. Nos. 60/702,202 and/or 60/713,322, supra. A coupler 1310 is affixed to the ultrasound probe 1304 through a straight slot formed in the housing 1306. The biopsy guide couples to a needle holder 1316 such that a biopsy needle 1318 is maintained in the scan plane of the ultrasound probe 1304. For the embodiment of FIG. 13, the biopsy guide 1310/1312 comprises two links hingeably coupled to allow the biopsy needle 1318 to have varying angles of attack into the lesion within the scan plane.

Preferably, the biopsy guide 1310/1312 is extendable in an outward direction such that the depth of the biopsy instrument into the scan plane (i.e., the downward distance from the linear transducer array within the scan plane in FIG. 13) can be varied, e.g., by having a telescoping/retracting capability. In still other embodiments, in a manner analogous to that disclosed in the commonly assigned U.S. Pat. No. 6,695,786, supra, a multi-link assembly having 3 or more links is provided for permitting a broader range of angular orientations of the biopsy needle 1116 within the scan plane. Also, such multi-link assembly would inherently provide a depth-varying functionality for moving the biopsy instrument to shallower and deeper depths in the scan plane. It is to be appreciated that many different mechanical configurations achieving similar mechanical goals would be apparent to one skilled in the art in view of the present disclosure and are within the scope of the embodiments, including embodiments with motorized positioners and needle insertion mechanisms.

Figure 14:
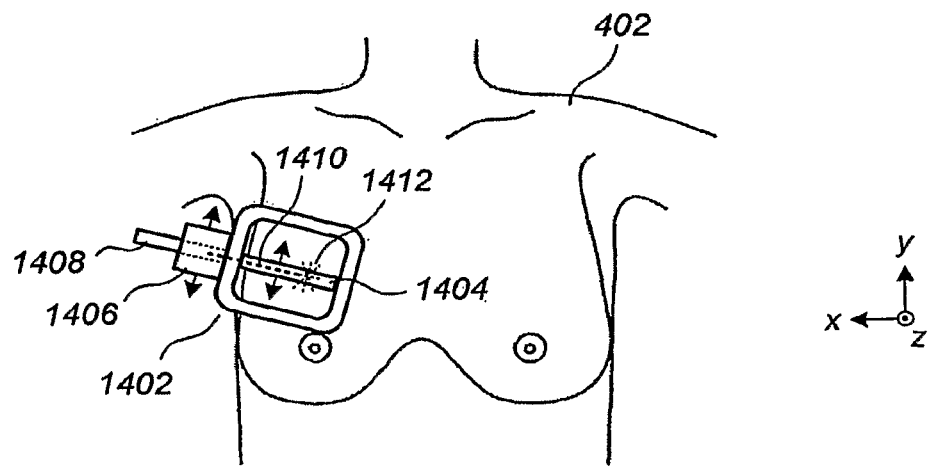
FIG. 14 illustrates a top view of a compression/scanning assembly and a biopsy guide attachment according to an embodiment.

FIG. 14 illustrates a top view of a smaller, specialized compression/scanning assembly 1402 including an integrated biopsy guide 1406 according to an embodiment. The size and trajectory of an ultrasound probe 1404 are substantially smaller, perhaps as small as three inches, for particularly performing percutaneous breast biopsies using the biopsy needle 1410 and needle holder 1408. The integrated biopsy guide 1406 is configured and adapted to restrict the biopsy needle 1410 to the scan plane of the ultrasound probe 1404, while allowing multiple depths and angles within the scan plan for attacking a breast lesion 1412 over which the ultrasound probe 1404 has been positioned. In one embodiment, the compression/scanning assembly 1402 is entirely handheld, while in other embodiments it is mechanically supported by a support arm.

Figure 15:
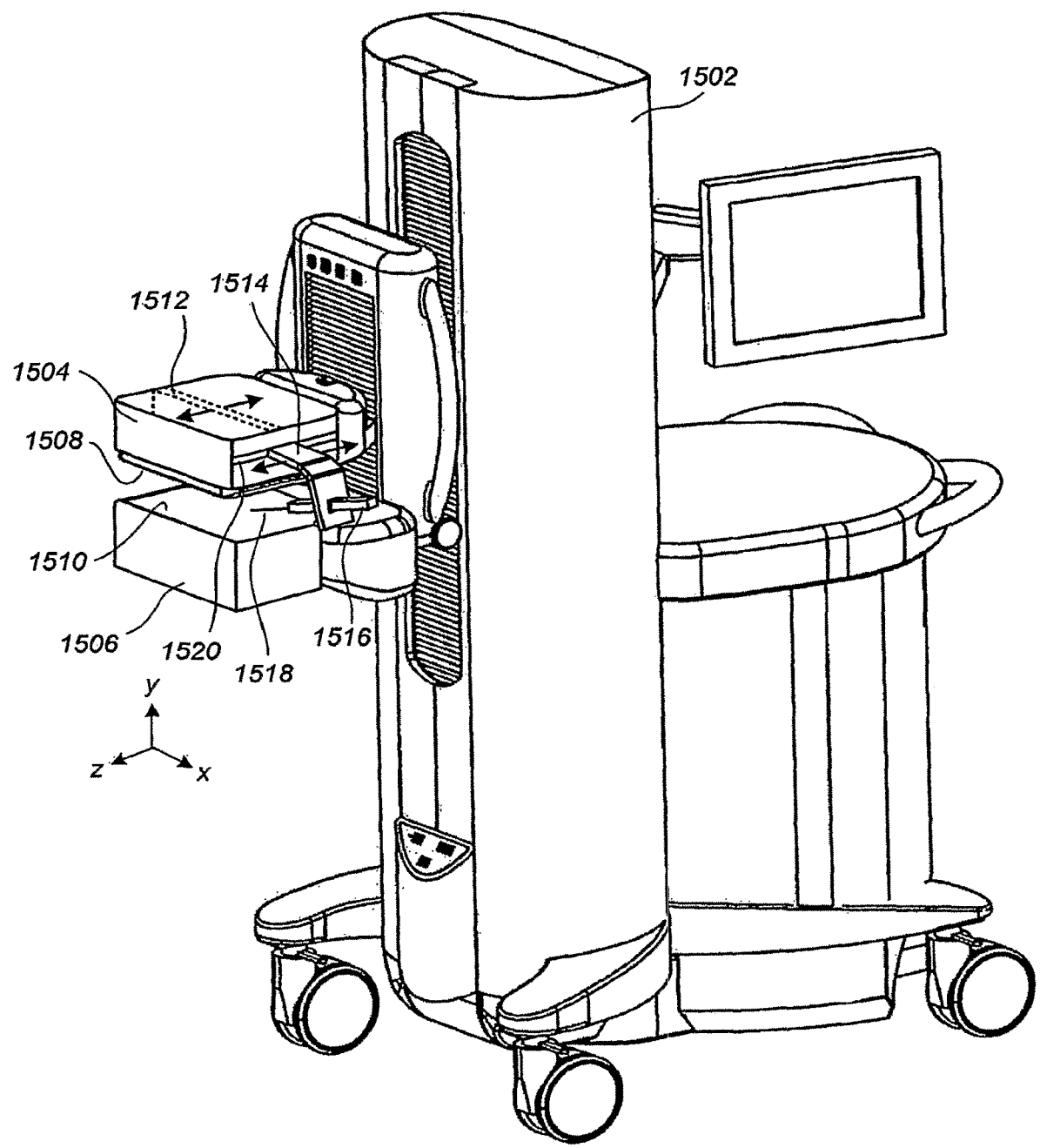
FIG. 15 illustrates a perspective view of a breast ultrasound scanning apparatus with biopsy guide attachment according to a preferred embodiment.

FIG. 15 illustrates a perspective view of a breast ultrasound scanning apparatus 1502 with biopsy guide attachment according to an embodiment. The apparatus comprises an upper compression/scanning assembly 1504 and a lower compression/scanning assembly 1506, the breast of an upright patient being inserted therebetween for scanning and/or biopsy (the patient is facing the −z axis). Upper compression/scanning assembly 1504 comprises a compressive surface 1508, such as a membranous sheet described supra, and a probe 1512 that is swept thereover in the z direction. A biopsy guide 1514 is affixed to the ultrasound probe 1512 through a slot 1520 as shown. The biopsy guide 1514 couples to a needle holder 1516 such that a biopsy needle 1518 is restricted to the scan plane of the ultrasound probe 1512 while allowing multiple depths and angles within the scan plan for attacking a breast lesion over which the ultrasound probe 1512 has been positioned. The lower compression/scanning assembly 1506 may simply comprise a compression plate 1510, or alternatively may be a duplicate of the upper compression/scanning assembly 1504 for allowing two-sided scans and other advantageous applications. In other embodiments, one or more aspects of the breast ultrasound scanning apparatus, with the exception of the biopsy guide attachment, can be found in the commonly assigned WO 2004/030523A2, which is incorporated by reference herein.

Figure 16:
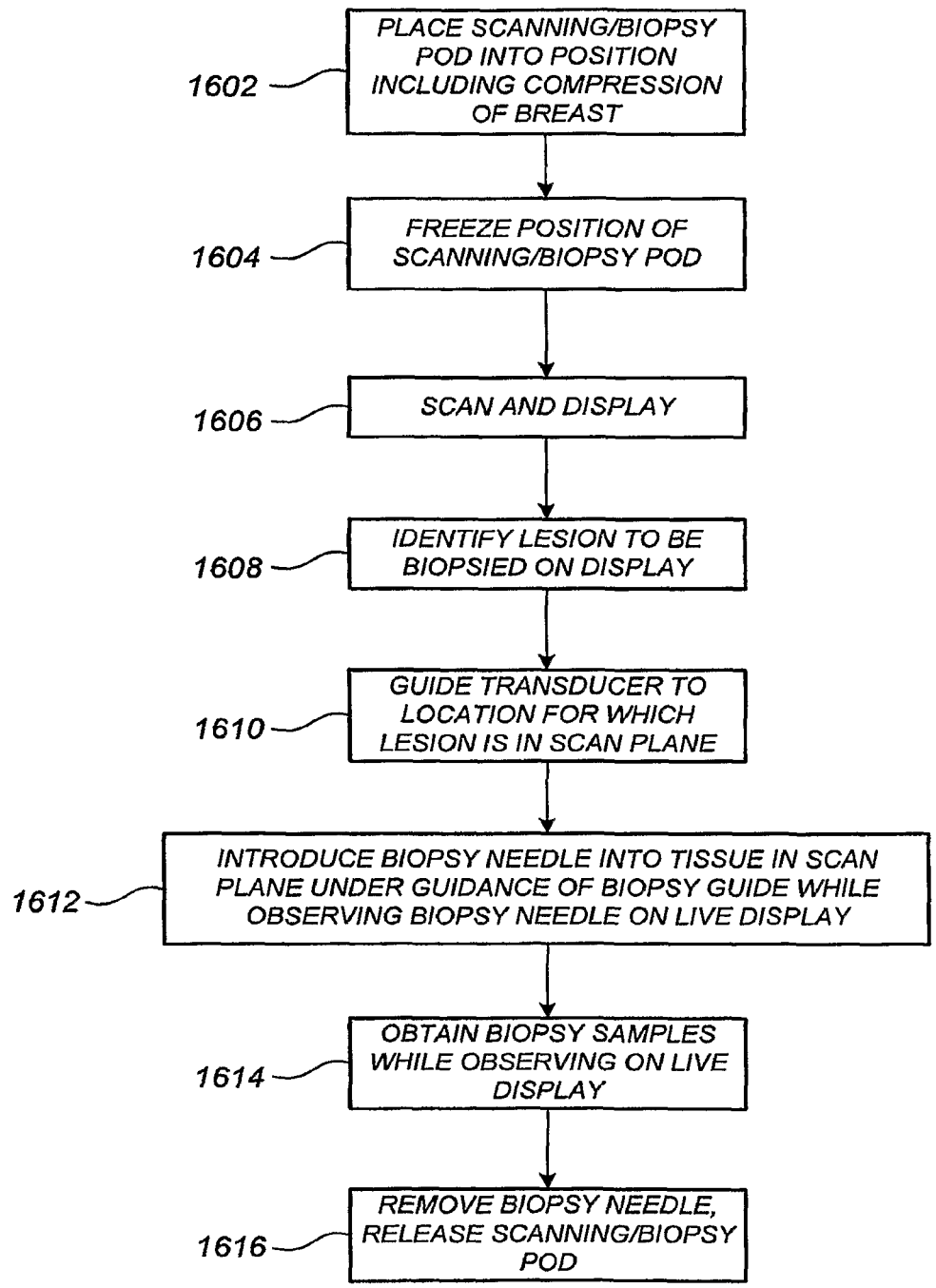
FIG. 16 illustrates ultrasound scanning and ultrasound-assisted breast biopsy according to an embodiment.

FIG. 16 illustrates ultrasound scanning and ultrasound-assisted breast biopsy according to an embodiment. As used hereinbelow, the term biopsy/scanning pod is used to refer to the compression/scanning assembly 1102 of FIG. 11 together with the attached biopsy guide attachment 1108, or to other compression/scanning assemblies such as those of FIG. 10, FIG. 13, and FIG. 14 together with similar biopsy guide attachments. At step 1602, the scanning/biopsy pod is compressibly positioned on the breast. Generally speaking, the curved contour of the scanning/biopsy pod will be positioned to follow the rib cage of the patient, with the scan plane (and therefore the plane of needle movement) being at least roughly in the head-to-toe direction, although a variety of other orientations are possible as well depending on the breast size, breast shape, lesion location, and other factors. Prior to step 1602, the breast is preferably wetted with a liquid or gel acoustic couplant. If the nipple of the breast protrudes or is recessed by substantial amounts, it should be generously wetted with a relatively large amount of couplant so that air pocket formation is avoided when the nipple is contacted by the membranous sheet.

At step 1604, the position of the scanning/biopsy pod is frozen in place using the above-described position-freezing capability. Notably, it is the overall housing of the scanning/biopsy pod that is frozen in place, and not the ultrasound transducer itself, which is still movable inside the scanning/biopsy pod. At step 1606, the breast is scanned to generate a three-dimensional volumetric representation thereof, and results therefrom are displayed to the radiologist. Any of a variety of different two-dimensional and three-dimensional images are displayed as may be required by the radiologist to properly identify, locate, and visualize the lesion and the surrounding tissue including, without limitation, thin-slice views, thick-slice views, maximum-intensity projection views, or other views as described in the commonly assigned US2003/0212327A1 and US2005/0171430A1, which are incorporated by reference herein. At step 1608, the lesion is identified by the radiologist.

At step 1610, the ultrasound transducer is guided until the lesion is located in the scan plane. The movement of the transducer can be fully automatic, semi-automatic, or hand-controlled by the radiologist (e.g., using buttons, mouse, joystick, etc.) without departing from the scope of the embodiments. At the end of step 1610, the plane of confinement of the biopsy needle corresponds to a live planar image of the scan plane being displayed, which includes the lesion.

At step 1612, the biopsy needle is introduced into the breast, under mechanical guidance of the biopsy guide and under visual monitoring by the radiologist using the live planar image. The movement of the biopsy needle may be fully automatic, semi-automatic, or hand-controlled by the radiologist, although at all times it is under visual observation by the radiologist because the needle is confined to the scan plane. For embodiments in which the biopsy needle is fully- or semi-automatically actuated, the controlling processor can be provided with image information from the scanned images from which the needle and the lesion can be segmented to facilitate control of the biopsy needle position. The rib cage can also be segmented and hardware or software limits/stops placed on the range of motion, to avoid accidental puncture of the underlying anatomy. Even for manually actuated embodiments in which the needle is guided and actuated by the radiologist, automated sensing and mechanical limiting can be used to avoid accidental punctures based on the relative positions of the lesion, needle, rib cage, etc., as detected from the real-time ultrasonically-obtained image information.

In another embodiment, predictive biopsy needle highlighting is provided on the user display in a manner analogous to that described in U.S. Pat. No. 6,695,786, supra. Regardless of the current position of the biopsy needle—even if it has not yet been inserted into the patient—a needle projection image is superimposed on the ultrasound display to represent the trajectory that the needle would have if it were to follow the exact direction in which it is currently pointing. Optionally, the "throw" of a spring-loaded biopsy needle can be marked on the needle projection image, representing the future needle depth when the spring-loaded trigger has been released.

At step 1614, biopsy samples are collected as the radiologist continues to monitor the display. As known in the art, where the lesion is hard, the biopsy needle is springably "shot" into the lesion using a spring-trigger mechanism. At step 1616, the biopsy needle is removed and the scanning/biopsy pod is released. It is to be appreciated that equivalent procedures using other compression/scanning assemblies, such as those having dual compression paddles (see FIG. 15, for example) are also within the scope of the embodiments.

Figure 17:
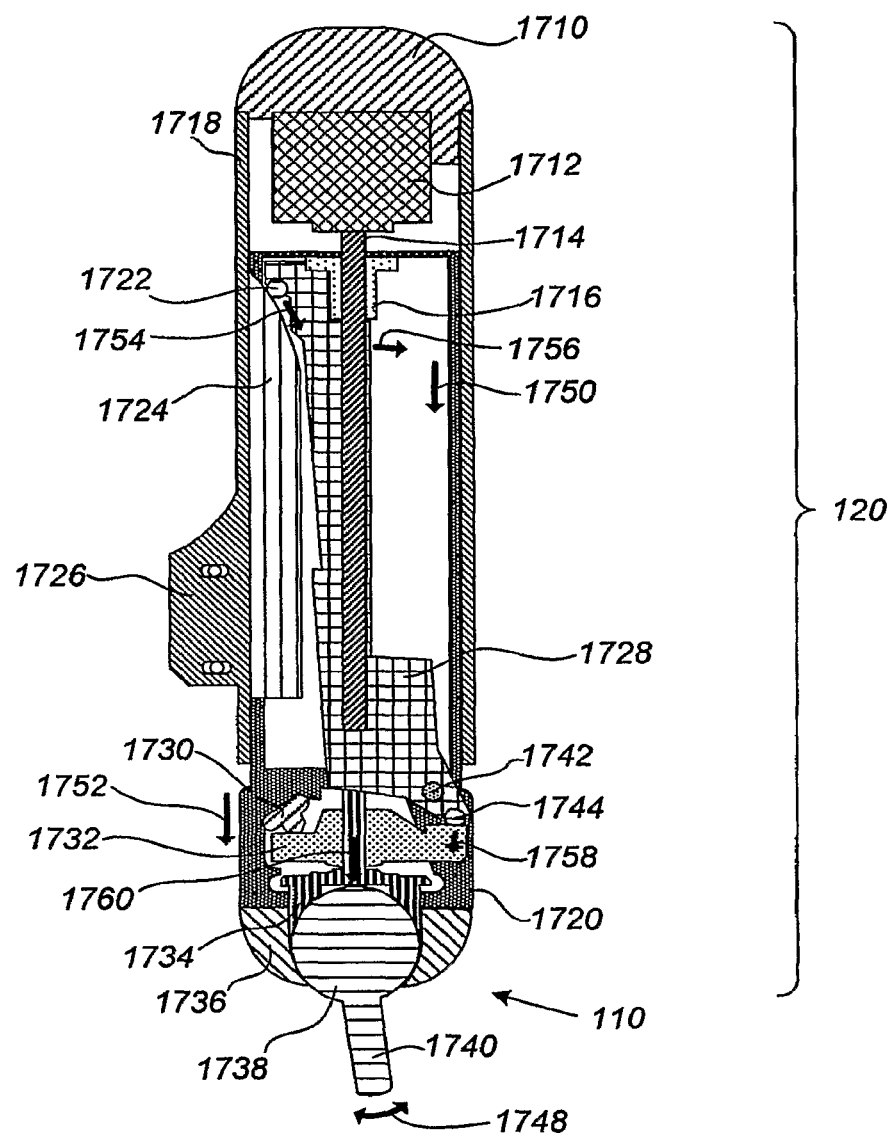
FIG. 17 illustrates a locking and actuating support column according to certain embodiments

FIG. 17 illustrates a locking and actuating support column according to certain embodiments. Column 120 includes ball joint 110 which is comprises of socket 1736, ball 1738 and member 1740. Compression/scanning assembly 108 of FIG. 1 is fixedly attached to member 1740 such that ball joint 110 provides assembly 108 with pitch, roll and yaw motions as indicated by arrow 1748. Socket 1736 is fixedly attached to lower housing 1720. Lower housing 1720 slides along the axis of column 120 within upper housing 1718. Upper housing 1718 is attached to cap 1710 to which arm 106 is attached via joint 142 as shown in FIG. 1. Alternatively, arm 106 can be attached via join 142 to flange 1726 which is part of upper housing 1718. Relative actuation between housings 1718 and 1720 is accomplished using stepper motor 1712 which is fixedly mounted on cap 1710. Motor 1712 turns lead screw 1714 which is engaged with nut 1716. Nut 1716 is fixedly mounted on the upper end of lower housing 1720. Thus stepper motor 1712 causes lower housing 1720 to move relative upper housing 1718 along the axis of column 120 in the direction indicated by arrows 1750 and 1752. According an embodiment, locking of ball join 110 is provided automatically as part of the actuation process through the use of ramp 1724 which is fixedly mounted on the inner wall of upper housing 1718 and which protrudes through a slot in lower housing 1720. When lower housing is pushed downwards by stepper motor 1712, roller 1722 rolls along ramp 1724 in a direction indicated by arrow 1754. Roller 1722 is attached to lever 1728 which is mounted to lower housing 1720 at pivot 1742. When roller 1722 moves along ramp 1724 in the direction indicated by arrow 1754, lever 1728 pivots and moves in directions indicated by arrows 1756 and 1758. Attached to lever 1728 is roller 1744 which pushes upon inner lever 1732 in the direction indicated by arrow 1758. Inner lever 1732 pivots on fulcrum 1730, and when pushed in the direction indicated by arrow 1758, pushes on ball clamp 1734 which in turn pushes on ball 1738 in the direction indicated by arrow 1760. In this way, due to the contour of ramp 1724, ball clamp 1734 is engaged with and automatically locks the movement of ball 1738 at the beginning portion of downward movement of inner housing 1720.

Figure 18:
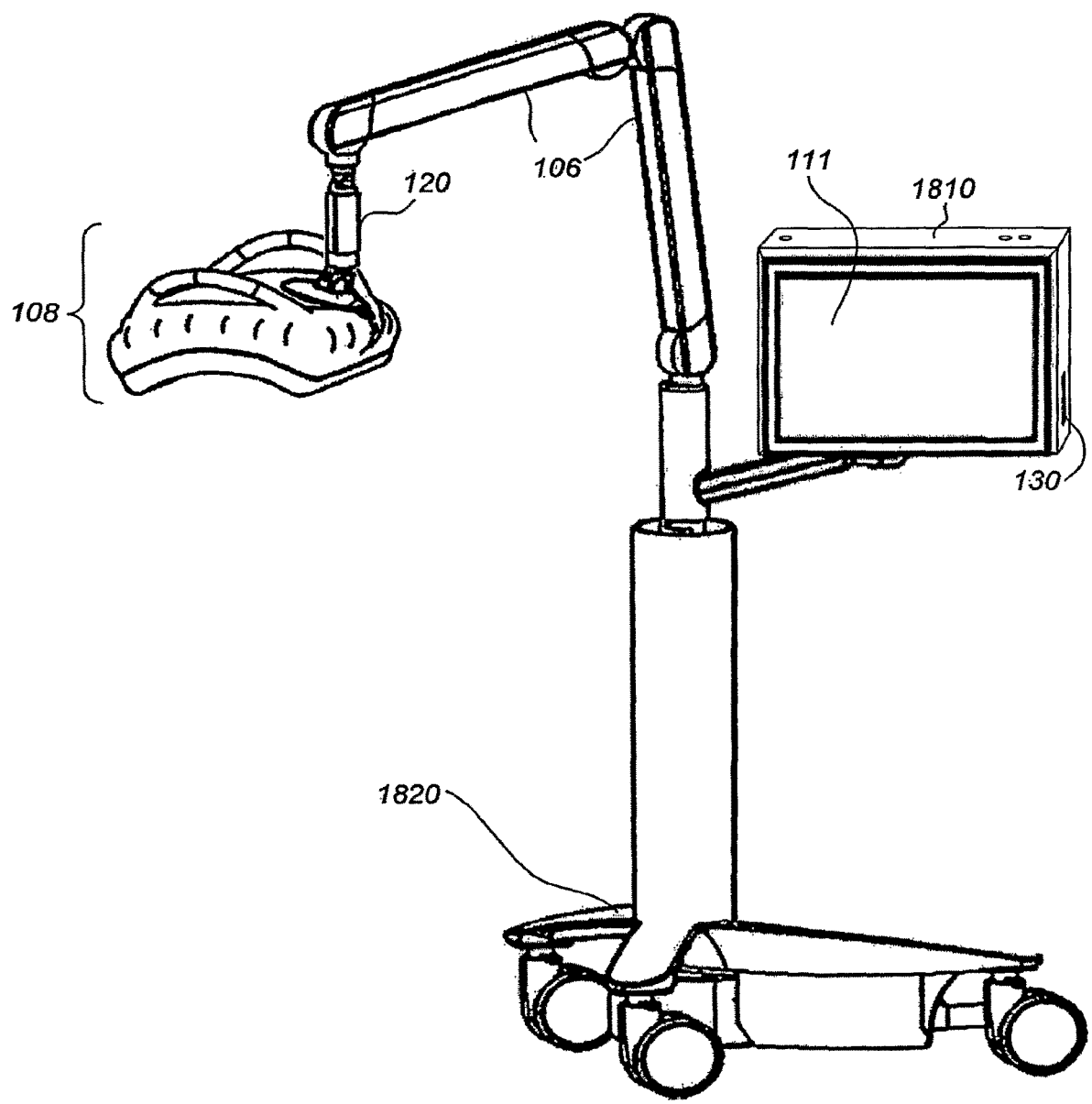
FIG. 18 illustrates a perspective view of a breast ultrasound scanning apparatus according to an alternative embodiment.

FIG. 18 illustrates a perspective view of a breast ultrasound scanning apparatus according to an alternative embodiment. Compression/scanning assembly 108 has integrated ultrasound electronics as described supra, thus allowing for a much more compact system. As mentioned, the integration of compact ultrasound electronics greatly decreases the path length between the beamformer and the transducer. Compact electronics also greatly reduced the need for large power supplies. Monitor 111 is also integrated with computer processor system 1810 which handles the user interface and data management and control functions. Processor system 1810 can be based on a laptop PC design or other small format computer platform such as a tablet PC, mini-box PC, thin-profile PC or all-in-one PC. processor system 1810 also integrates sensor 130 as described supra. The ultrasound scanning apparatus is mounted on wheel assembly 1820 for ease of positioning and flexibility of use.

Figure 19:
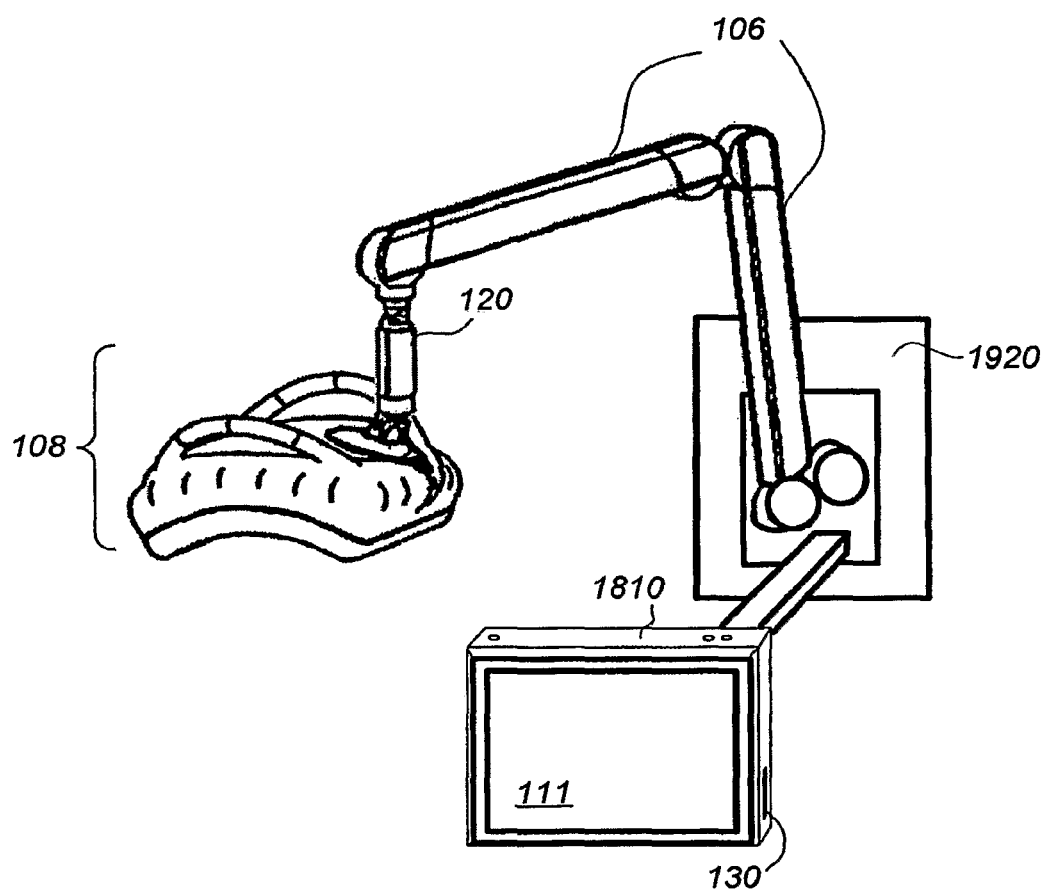
FIG. 19 illustrates a perspective view of a wall mounted breast ultrasound scanning apparatus according to a further alternative embodiment.

FIG. 19 illustrates a perspective view of a wall mounted breast ultrasound scanning apparatus according to a further alternative embodiment. The ultrasound scanning apparatus of FIG. 19 is similar to that shown and describe in FIG. 18, except that it is wall mounted on mount 1920 instead of wheel mounted. Wall mounting advantageously saves floor space and is preferred for some settings.

Figure 20:
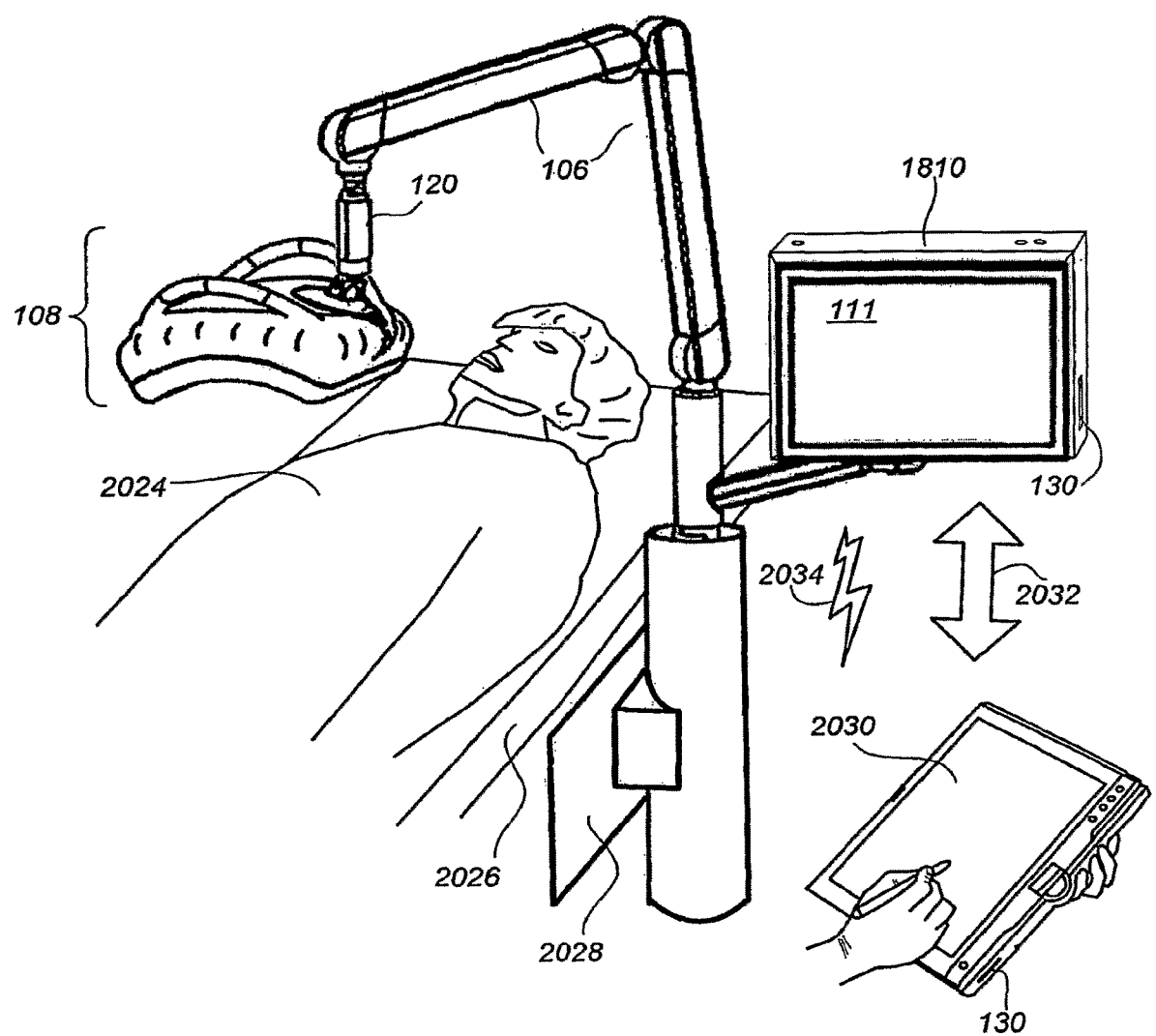
FIG. 20 illustrates a perspective view of a chair or bed-mounted breast ultrasound scanning apparatus according to further alternative embodiments.

FIG. 20 illustrates a perspective view of a chair or bed-mounted breast ultrasound scanning apparatus according to further alternative embodiments. The ultrasound scanning apparatus of FIG. 20 is similar to that shown and described in connection with FIGS. 18-19, except that is mounted on bed 2026 via mount 2028. Bed 2026 may alternatively be a dentist-style chair for the comfort and flexibility of positioning of patient 2024. According to yet further embodiments, computer processing system 1810 can be a tablet-type PC 2030. The tablet-type PC 2030 is preferably removable and dockable as indicated by arrow 2032. While undocked, PC 2030 can communicate with the rest of the scanning apparatus via Bluetooth, Wi-Fi or other suitable wireless communication technology, tablet-type PC 2030 provides greater flexibility in the user interface and allows for the operator to more easily share the images with the patient or with other personnel such as a radiologist so as to aid in decision making.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be appreciated that any of a variety of different frame assemblies can be used that position, tension, and otherwise manipulate the membranous sheet, whether the membranous sheet is permanently used and re-used for different patients or is disposable for each patient, without departing from the scope of the present teachings. By way of further example, while in the above-described embodiments the biopsy guide is translatable in conjunction with the ultrasound transducer, in other embodiments the biopsy guide is fixably coupled to the housing around the ultrasound transducer, the biopsy instrument only being maintained in the scan plane when the ultrasound transducer is positioned adjacent to the biopsy guide within the housing. In still other embodiments, the biopsy guide is not fixably attached to the ultrasound probe, yet is also decoupled from the ultrasound transducer, i.e., the ultrasound probe and the biopsy guide are independently translatable relative to the housing. By way of even further example, although described primarily in terms of breast ultrasound and percutaneous biopsy, one or more of the above-described embodiments are readily applicable and/or adaptable for compressive ultrasonic imaging and/or percutaneous biopsy for the arm, the leg, the neck, the abdomen, or other human or animal body part.

By way of still further example, in other embodiments there are provided dual scanning pods, i.e., dual compression/scanning assemblies (optionally with biopsy attachments) mounted on a common support arm in a butterfly-wing configuration. The dual scanning pods are configured such that they can be simultaneously placed over both breasts for simultaneous scanning. By way of even further example, in other embodiments the provided scanning pod is equipped to have the biopsy guide attachment placed on either side of the transducer, and/or to have two biopsy guides simultaneously attached to both sides of the transducer. By way of still further example, although embodiments are described supra in the context of linear ultrasound transducers, it is to be appreciated that other transducer types including 1.25D, 1.5D, and 2D transducers can be used without departing from the scope of the embodiments. Therefore, reference to the details of the embodiments are not intended to limit their scope.

What is claimed is:

1. An apparatus for ultrasonically scanning a tissue sample, comprising:
   an ultrasound transducer;
   a rigid frame including a first set of opposing sides and a second set of opposing sides, the first set of opposing sides having a curved shape and the second set of opposing sides being non-arcuate; and
   a single continuous membranous sheet disposed across the rigid frame and configured to compress the tissue sample, said ultrasound transducer comprising a lower face contacting a top of said membranous sheet and ultrasonically scanning the tissue sample therethrough, said top of said membranous sheet configured for direct contact with said ultrasound transducer, and said membranous sheet having a bottom configured for direct contact with the tissue sample;
   wherein said ultrasound transducer is movable in a trajectory during the ultrasonic scan, and further wherein at least one of the lower face of the ultrasound transducer and the trajectory is curved so as to create a generally curved scanned surface, said membranous sheet of uniform composition and at least partially porous to a liquid or gel acoustic couplant, the membranous sheet exerting a net force in a chestward direction of an underlying rib cage during the ultrasonic scan.

2. The apparatus of claim 1, said tissue sample being disposed intermediate the rib cage and the membranous sheet during the ultrasonic scan such that the tissue sample is compressed chestward in an at least partially conformal manner toward the underlying rib cage.

3. The apparatus of claim 2 wherein said rigid frame, ultrasonic transducer, and membranous sheet form part of an ultrasonic scanning system, wherein the ultrasonic scanning system has a spring constant in a direction perpendicular to the underlying rib cage of less than 100 pounds per inch.

4. The apparatus of claim 3 wherein the spring constant is less than about 25 pounds per inch.

5. The apparatus of claim 4 wherein the spring constant is less than about 2 pounds per inch.

6. The apparatus of claim 3 wherein the ultrasonic scanning system further comprises a support arm moveably attached to said rigid frame so as to allow a plurality of directions of movement of the rigid frame thereby allowing for positioning of the membranous sheet upon the tissue sample.

7. The apparatus of claim 6 wherein one or more of the directions of movement can be substantially restricted following positioning of the membranous sheet upon the tissue sample.

8. The apparatus of claim 7 wherein the support arm comprises at least one joint and is attached to the rigid frame using a ball joint and wherein the one or more directions of movement are substantially restricted by locking the ball joint and the at least one joint of the support arm.

9. The apparatus of claim 6 wherein the spring constant is primarily attributable to flexibility in the support arm, the rigid frame, and one or more interconnecting joints.

10. The apparatus of claim 6 further comprising an actuator mechanically coupled to said support arm and said rigid frame and arranged so as to move the rigid frame in a direction towards the underlying rib cage so as to increase pressure upon the tissue sample by the membranous sheet.

11. The apparatus of claim 10 wherein the pressure upon the tissue sample by the membranous sheet is equivalent to between 4 and 12 pounds of force.

12. The apparatus of claim 11 wherein the pressure upon the tissue sample by the membranous sheet is equivalent to about 8 pounds of force.

13. The apparatus of claim 1 wherein the membranous sheet is conformally aligned with the rib cage.

14. The apparatus of claim 1 wherein the generally curved scanned surface is achieved at least in part by the lower face of the ultrasound transducer being curved.

15. The apparatus of claim 1 wherein the generally curved scanned surface is achieved at least in part by the ultrasound transducer being moveable in the curved trajectory.

16. The apparatus of claim 1 wherein the frame further including a guide structure, and wherein the ultrasound transducer is movable in the trajectory between the second set of opposing sides and along the curved shape via the guide structure during the ultrasonic scan so as to create the generally curved scanned surface.

17. The apparatus of claim 1 wherein least one of the lower face of the ultrasound transducer and the trajectory has a radius of curvature between about 6 inches and 36 inches along a subtended arc between about 45 degrees and 135 degrees.

18. The apparatus of claim 1 wherein least one of the lower face of the ultrasound transducer and the trajectory has a radius of curvature between about 8 and 12 inches along a subtended arc between about 45 degrees and 135 degrees.

19. The apparatus of claim 1 further comprising said membranous sheet being wetted with the acoustic couplant facilitating acoustic coupling between said ultrasound transducer and the tissue sample, wherein said membranous sheet is substantially porous with respect to the acoustic couplant and discourages the presence of air bubbles therein between said ultrasound transducer and said tissue sample.

20. The apparatus of claim 1 wherein said ultrasound transducer is a linear transducer comprising a plurality of elements oriented to be substantially perpendicular to said trajectory during the ultrasonic scan.

21. The apparatus of claim 1 further comprising a biopsy guide configured and positioned to maintain a biopsy instrument in a scan plane of the ultrasound transducer for facilitating a percutaneous biopsy of a lesion located in said scan plane.

22. The apparatus of claim 21 wherein said biopsy guide is coupled to move with said ultrasound transducer along said trajectory, whereby said biopsy instrument can be maintained in said scan plane for any position of said ultrasound transducer along said trajectory.

23. The apparatus of claim 21 wherein said biopsy guide is removable from the apparatus.

24. The apparatus of claim 21 wherein said biopsy guide comprises a multi-link assembly permitting different angular orientations of the biopsy instrument within the scan plane.

25. The apparatus of claim 21 wherein said biopsy guide and biopsy instrument are motor-actuated under control of a processor, said processor being further coupled to receive image information derived from said ultrasonic scan of the tissue sample with the ultrasonic transducer.

26. The apparatus of claim 1 further comprising a support arm moveably attached to the rigid frame on a first end and attached to a wall on a second end.

27. The apparatus of claim 1 further comprising a support arm moveably attached to the rigid frame on a first end and attached on a second end to a piece of furniture upon which a patient is disposed.

28. The apparatus of claim 1 further comprising a removable monitor for interfacing with an operator who operates said ultrasonic transducer.

29. The apparatus of claim 28 wherein the removable monitor is part of a tablet-type PC that when removed is capable of wireless communication.

30. The apparatus of claim 1 further comprising a sensor for verifying an identity of an operator who operates said ultrasonic transducer.

31. The apparatus of claim 1 further comprising one or more sensors to monitor an amount of pressure being applied to the tissue sample.

32. A method for ultrasonically scanning a tissue sample comprising the steps of:
compressing the tissue sample with a net downward force in a chestward direction toward an underlying rib cage with a first side of a single membranous sheet disposed across a rigid frame, the first side of the membranous sheet directly contacting the tissue sample;
ultrasonically scanning the tissue sample through the membranous sheet by contacting an ultrasonic transducer with a second side of the membranous sheet and moving said ultrasonic transducer so as to create a generally curved scanned surface, the second side of the membranous sheet directly contacting the ultrasonic transducer during the scanning, said membranous sheet of uniform composition an comprised of one or more of a fabric and a vented membrane and at least partially porous to a liquid or gel acoustic couplant;
wherein the rigid frame includes a first set of opposing sides and a second set of opposing sides, the first set of opposing sides having a curved shape and the second set of opposing sides being non-arcuate.

33. The method of claim 32 wherein the generally curved scanned surface is achieved at least in part by a lower face of the ultrasound transducer being generally arcuate shaped and/or by the ultrasound transducer being moveable in a generally arcuate trajectory.

34. The method of claim 32 wherein the first side of the membranous sheet directly contacts a nipple of the tissue sample and compresses the tissue sample with the net downward force from the nipple chestward to the underlying rib cage during the scanning.

35. The method of claim 34 wherein the membranous sheet directly contacts a front centerpoint of the nipple during the scanning, and wherein the generally curved scanned surface is ellipsoidal.

36. The method of claim 32 wherein the membranous sheet is tautly disposed across the rigid frame.

37. The method of claim 36 wherein the rigid frame is moveably attached to a support arm so as to allow a plurality of directions of movement of the rigid frame thereby allowing for positioning of the membranous sheet upon the tissue sample, the support arm having at least one joint.

38. The method of claim 32 wherein the arcuate shape has a radius of curvature between about 6 inches and 36 inches along a subtended arc between about 45 degrees and 135 degrees.

39. The method of claim 38 wherein the arcuate shape has a radius of curvature between about 8 and 12 inches along a subtended arc between about 45 degrees and 135 degrees.

40. The method of claim 32 further comprising the step of wetting the membranous sheet with the acoustic couplant facilitating acoustic coupling between said ultrasonic transducer and the tissue sample, wherein the membranous sheet is substantially porous with respect to the acoustic couplant and discourages the presence of air bubbles therein between said ultrasonic transducer and said tissue sample.

41. The method of claim 32 wherein the ultrasonic transducer is a linear transducer oriented to be substantially perpendicular to an arcuate trajectory during the ultrasonic scan.

42. The method of claim 32 wherein the step of compressing comprises applying a pressure with a scanning system including the membranous sheet and the ultrasonic transducer, the scanning system having an effective spring constant in a direction perpendicular to the underlying rib cage of less than 100 pounds per inch.

43. The method of claim 42 wherein the effective spring constant is less than about 25 pounds per inch.

44. The method of claim 32 further comprising the steps of:
positioning the membranous sheet so as to be generally aligned with the tissue sample;
substantially restricting movement of the membranous sheet in at least one direction, wherein said step of positioning is carried out prior to said steps of substantially restricting and compressing.

45. The method of claim 44 wherein said step of substantially restricting is carried out as the compressing step initiates.

46. The method of claim 32 wherein the tissue sample is compressed by the membranous sheet with a force of between 4 and 12 pounds.

47. The method of claim 46 wherein the tissue sample is compressed by the membranous sheet with a force of about 8 pounds.

48. The method of claim 32 further comprising the step of verifying an identity of an operator of the ultrasonic transducer with one or more sensors.

* * * * *